US00PP33455P2

(12) United States Plant Patent
Pineau

(10) Patent No.: US PP33,455 P2
(45) Date of Patent: Sep. 7, 2021

(54) ***PHYSOCARPUS* PLANT NAMED 'MINBLA3'**

(50) Latin Name: *Physocarpus opulifolius*
Varietal Denomination: MINBLA3

(71) Applicant: Hortival Diffusion SAS, Beaufort en Valee (FR)

(72) Inventor: Patrick Pineau, Saint Mathurin sur Loire (FR)

(73) Assignee: Hortival Diffusion SAS

( * ) Notice: Subject to any disclaimer, the term of this patent is extended or adjusted under 35 U.S.C. 154(b) by 0 days.

(21) Appl. No.: 16/989,750

(22) Filed: Aug. 10, 2020

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./226
See application file for complete search history.

(56) References Cited

PUBLICATIONS

Pepiniers Minier website. https://www.pepinieres-minier.fr/de/produit/physocarpus-opulifolius-black-light-r-minbla3-cov. Accessed Feb. 10, 2021. 4 pages. (Year: 2020).*

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Physocarpus* cultivar named 'MINBLA3' is disclosed, characterized by medium to large dark foliage (upper and lower surfaces) on vigorous plants. Flowers are light pink with a darker pink flushing. Plants produce bright red fruit. The new variety is a *Physocarpus*, normally produced as an outdoor garden or container plant.

6 Drawing Sheets

Latin name of the genus and species: *Physocarpus opulifolius.*
Variety denomination: 'MINBLA3'.

BACKGROUND OF THE INVENTION

The new *Physocarpus* cultivar is a product of a planned breeding program conducted by the inventor, in La Menitre, France. The crossing resulting in this new variety was made during May of 2008.

The new *Physocarpus* 'MINBLA3' resulted from the crossing of the seed parent, an unnamed, unpatented proprietary *Physocarpus opulifolius* referred to as '11078' with the pollen parent, *Physocarpus opulifolius* 'Mindia', U.S. Plant Pat. No. 16,371. The new variety was identified as a potentially interesting selection in August of 2011, at a commercial nursery in La Menitre, France.

Asexual reproduction of the new cultivar 'MINBLA3' by softwood cuttings was first performed during August of 2011, at commercial greenhouse in La Menitre, France. Subsequent propagation has shown that the unique features of this cultivar are stable and reproduced true to type in 9 successive generations. Date of first sale was Oct. 1, 2019, occurring in France. This sale was made directly by the inventor or one who obtained the claimed invention directly or indirectly from the inventor. This sale and all public disclosures made between Oct. 1, 2019 and the filing of this application fall within the exception allowed under 102(b)(1).

SUMMARY OF THE INVENTION

The cultivar 'MINBLA3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MINBLA3' These characteristics in combination distinguish 'MINBLA3' as a new and distinct *Physocarpus* cultivar:

1. Very dark purple foliage (under and upper surfaces),
2. Vigorous growth,
3. Medium to large foliage size,
4. Light pink flowers with darker pink flushing.
5. Bright red fruit.

PARENT COMPARISON

Plants of the new cultivar 'MINBLA3' are similar to plants of the seed parent, in most horticultural characteristics, however, plants of the new cultivar 'MINBLA3' differ in the following:

1. 'Minbla3' produces a darker purple upper mature leaf color than '11078', which has a purple and green leaf color.
2. 'Minbla3' produces a purple-red under surface mature leaf color compared to the green purple lower surface color of '11078'.
3. 'Minbla3' produces a larger leaf than '11078'.
4. 'Minbla3' produces red fruit, fruit of '11078' is pink and green.

Plants of the new cultivar 'MINBLA3' are similar to plants of the pollen parent, in most horticultural characteristics, however, plants of the new cultivar 'MINBLA3' differ in the following:

1. Young foliage of 'Minbla3' is colored purple, young foliage of 'Mindia' is orange.
2. 'Minbla3' produces a darker purple upper mature leaf color than 'Mindia', which has a purple and green mature leaf color.

COMMERCIAL COMPARISON

Plants of the new cultivar 'MINBLA3' can also be compared to the commercial variety *Physocarpus opulifolius* 'Minall2' U.S. Plant Pat. No. 29,892.The varieties are similar in most horticultural characteristics; however 'MINBLA3' differs in the following:

1. 'Minbla3' is more vigorous than 'Minall2'.
2. Young foliage of 'Minbla3' is dark purple, young leaf color of 'Minall2' is bright red.
3. 'Minbla3' produces a darker purple mature leaf color than 'Minall2' (under and upper surfaces)
4. 'Minbla3' produces a larger leaf size than 'Minall2'.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of new *Physocarpus opulifolius* 'Minbla3'. Photographs provided by the breeder.

FIG. 1 illustrates in full color new growth and flowers on *Physocarpus opulifolius* 'Minbla3' during June in La Menitre, France. Age of the plant is approximately 2 years.

FIG. 2 illustrates in full color the typical plant habit of the new variety in a container. Container size is approximately 2 gallons, plant age about 20 months. The plant was grown in La Menitre, France and photographed during June.

DETAILED BOTANICAL DESCRIPTION

Figure 1:
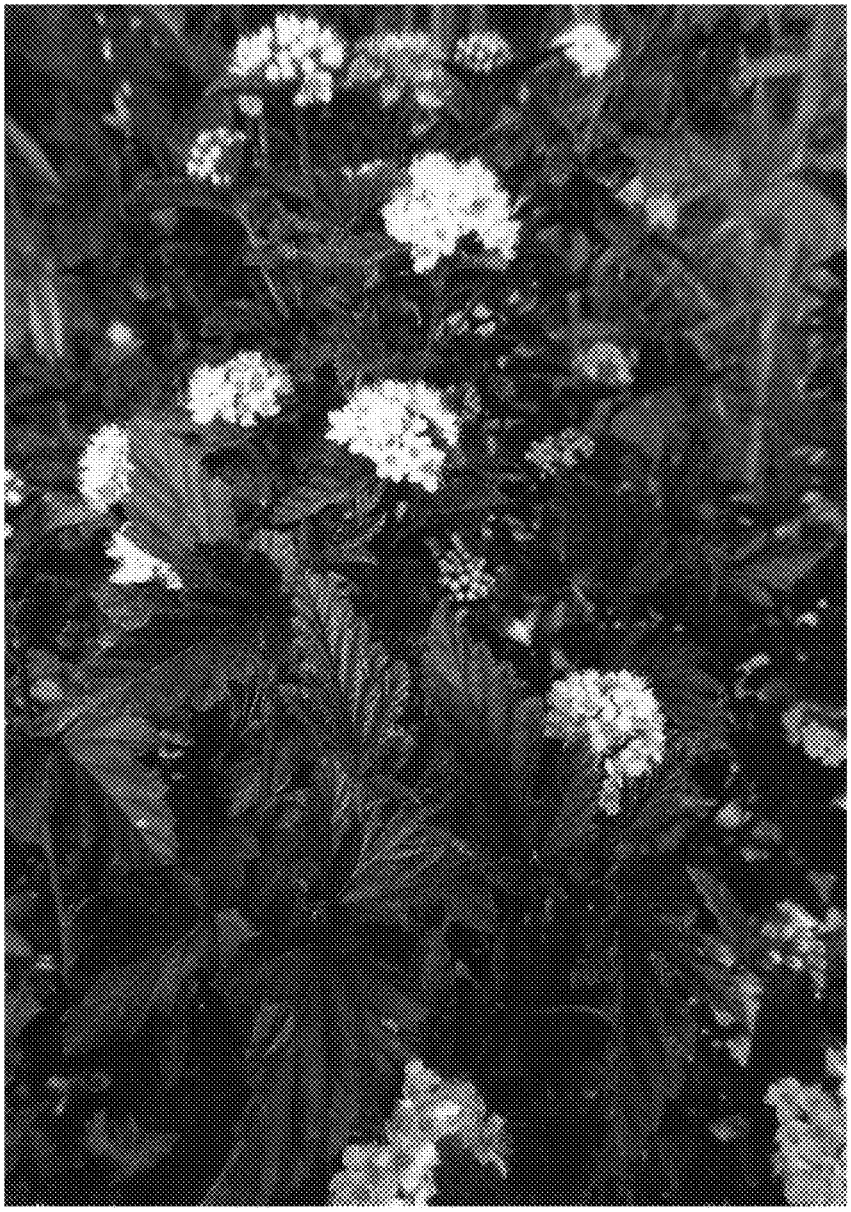
Figure 2:
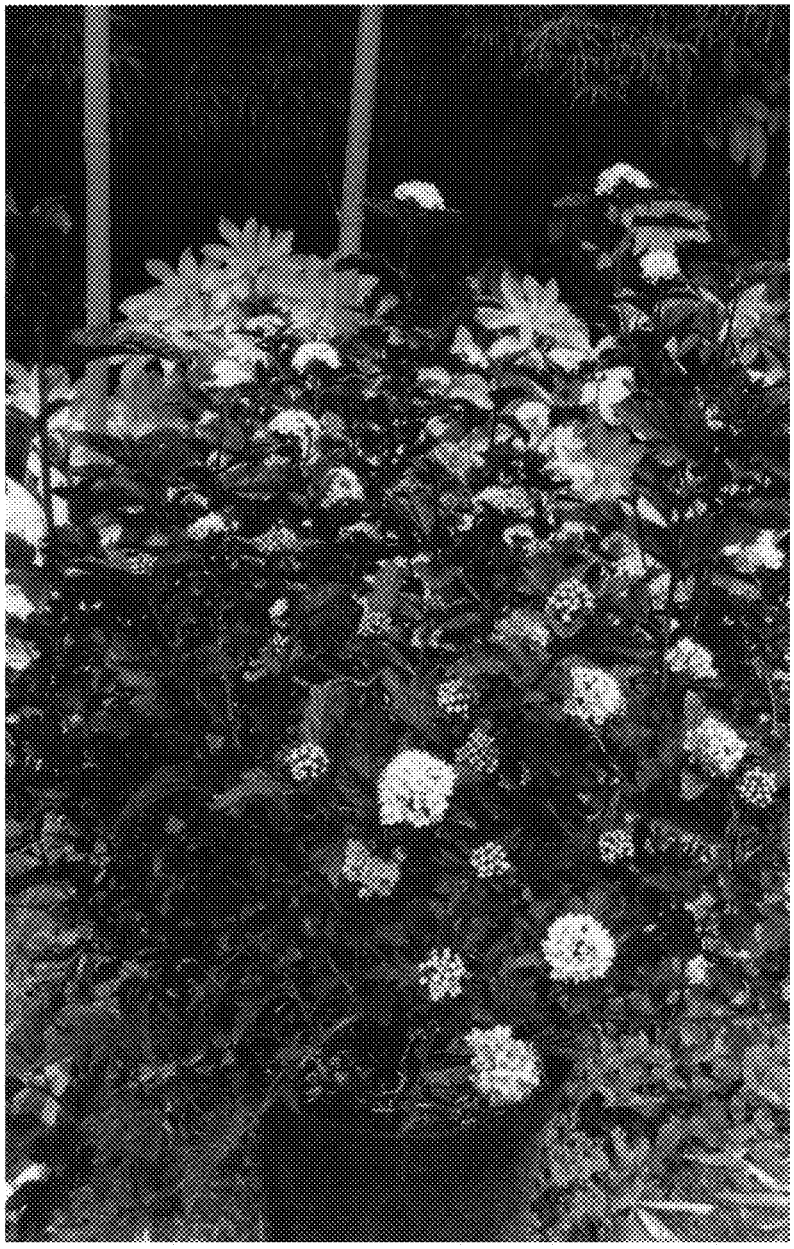
Figure 3:
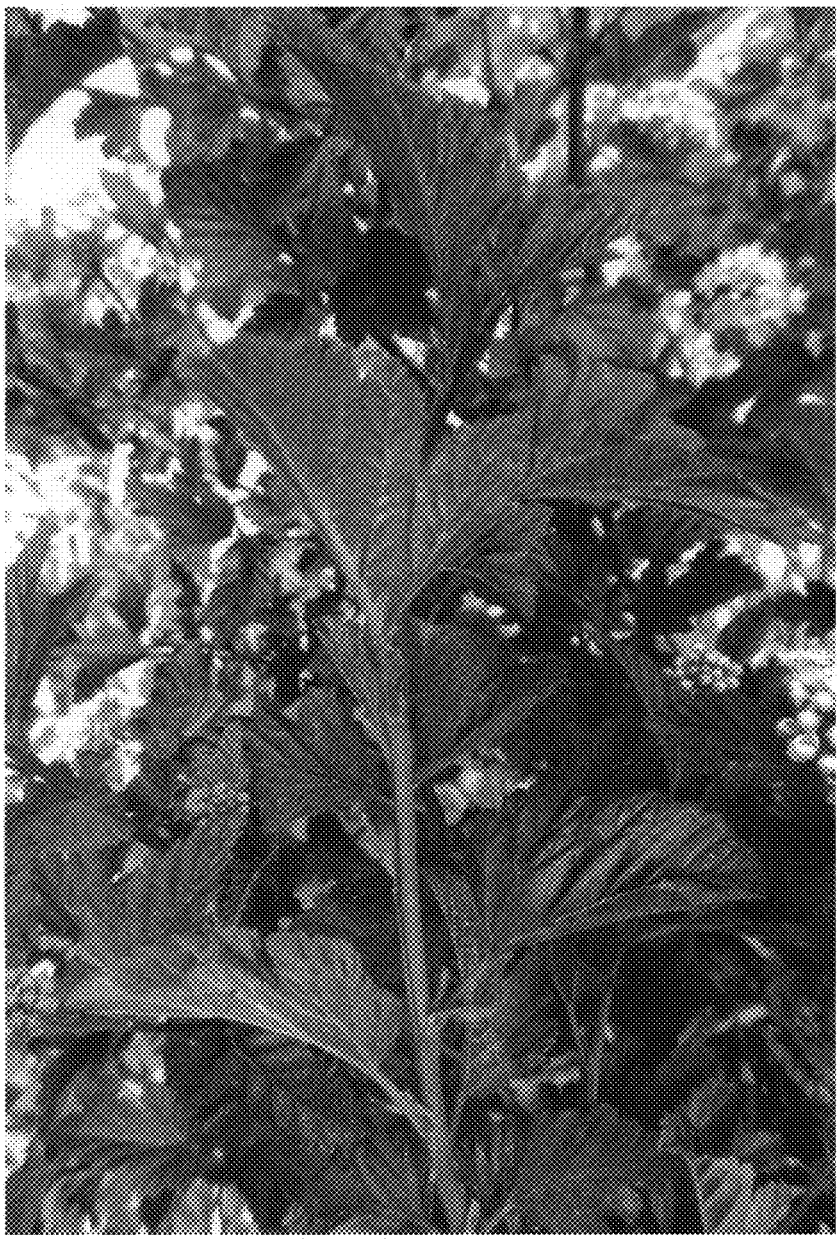
FIG. 3 illustrates in full color a closeup of the lower surface of the foliage of the new variety.
Figure 4:
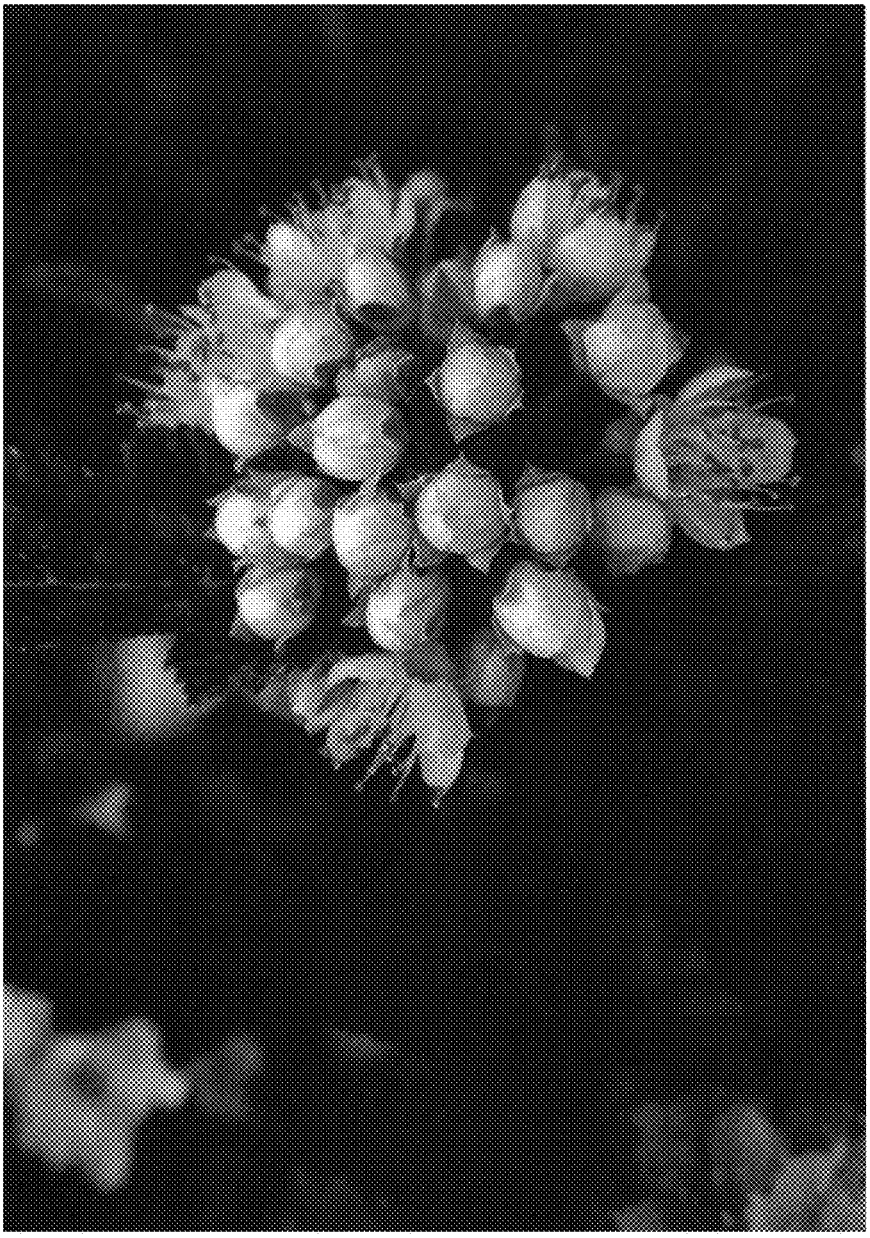
FIG. 4 illustrates in full color a closeup of the flower buds and opening flowers of the new variety. The photograph was taken in June.
Figure 5:
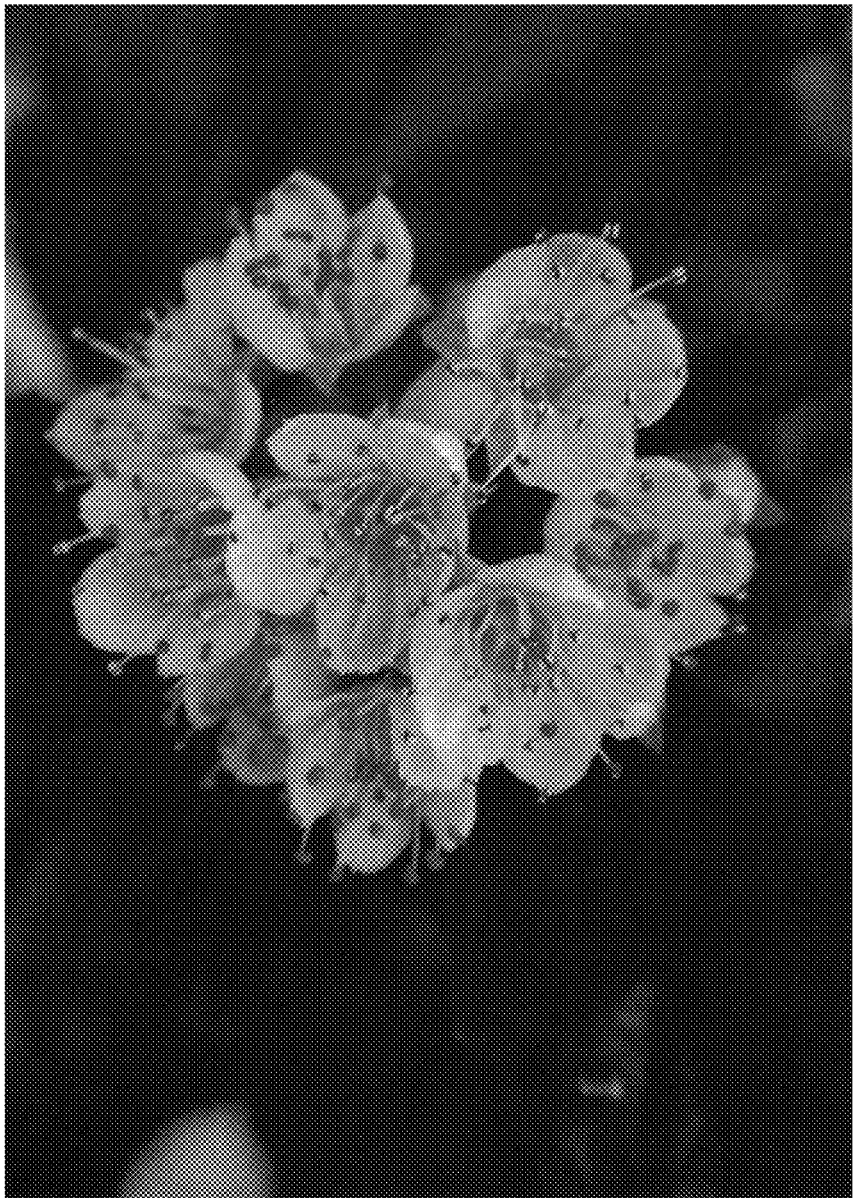
FIG. 5 illustrates in full color a closeup of the open flowers of the new variety. The photograph was taken in June.
Figure 6:
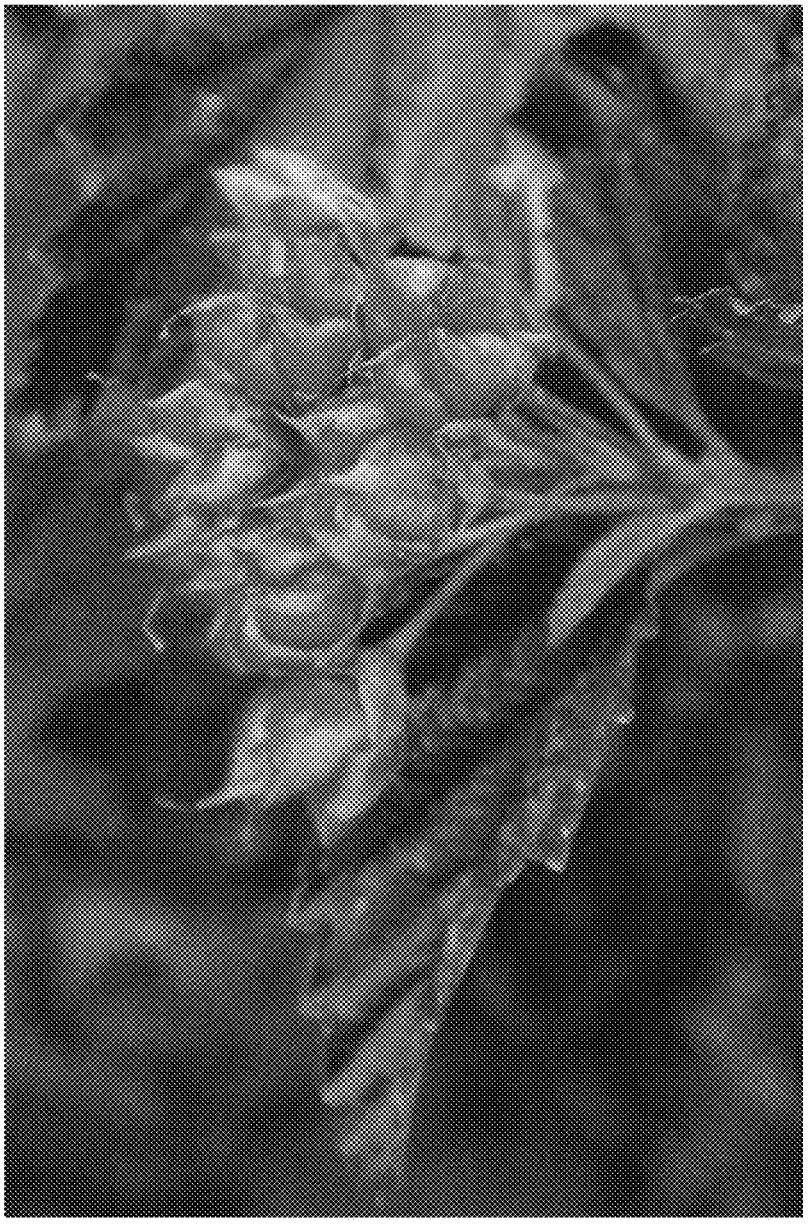
FIG. 6 illustrates in full color a closeup of the fruit of the new variety. The photograph was taken in August.

In the following description, color references are made to The Royal Horticultural Society Colour Chart 2007 except where general terms of ordinary dictionary significance are used. The following observations and measurements describe 'MINBLA3' plants grown outdoors in Salem, Oreg. The plants were approximately 2 years old grown in 5 gallon containers. Measurements and numerical values represent averages of typical plant types.

Botanical classification: *Physocarpus opulifolius* 'MINBLA3'.

PROPAGATION

Time to initiate roots: About 24 days at approximately 25° C.

Root description: Fine, and freely branching, both fibrous and fleshy. Colored near RHS 200D, tips near Yellow-White 158D.

Time to produce a liner: About 60 days at 24° C.

PLANT

Plant type: Flowering deciduous perennial shrub.

Age of plant described: Approximately 2 years old.

Growth habit: Upright and outwardly spreading at acute angles.

Pot size of plant described: 5 gallon pot.

Height: Approximately 50 cm to top of foliage. 150 cm at maturity.

Plant spread: Approximately 70 cm.

Growth rate: Rapid, vigorous.

Plant vigor: Strong.

Branching characteristics: Free, basal branching when pinched.

Length of primary lateral branches: Average range 30-60 cm.

Diameter of lateral branches: Approximately 5 mm.

Quantity of lateral branches: Average range, 20-30 main lateral branches.

Stem:

*Appearance*.—Rounded, slight pentagonal shape.

*Aspect/angle*.—Most branches at acute angles, about 15°. Lowermost outer branches about 70°.

*Strength*.—Strong.

*Texture*.—New stems: glabrous. Oldest stems: Peeling.

*Stem color*.—New stems: Near RHS Greyed-Purple N186C. Oldest stems: Near RHS Greyed-Orange N167D. Peeling bark colored near Brown 200A.

Internode length: Average range 3 to 6 cm.

FOLIAGE

Leaf:

*Arrangement*.—Alternate, single.

*Average length*.—Approximately 8.5 cm.

*Average width*.—Approximately 8.0 cm.

*Shape of blade*.—Broad ovate. Tri-lobed.

*Apex*.—Acute.

*Base*.—Cordate.

*Attachment*.—Stalked.

*Margin*.—Serrate-dentate.

*Texture of top surface*.—Smooth.

*Texture of bottom surface*.—Smooth.

*Pubescence*.—None.

*Color*.—Young foliage upper side: Near RHS Greyed-Purple N186C, with overall flush N186B. Young foliage under side: Near RHS Greyed-Purple N186C, with overall flush N187B. Mature foliage upper side: Near RHS Greyed-Purple N186A. Mature foliage under side: Near RHS Brown 200B, with over all flush Greyed-Purple 187A. Fall foliage: Not observed different in color from mature foliage.

*Venation*.—Type: Palmate. Venation color upper side: Near RHS Grey-Brown 199D. Uppermost veins Greyed-Purple 187A. Venation color under side: Near RHS Greyed-Purple 187C, upper veins near Greyed-Yellow 161D flushed 187C.

*Petiole*.—Average Length: Approximately 2.1 cm. Diameter: Approximately 3 mm. Petiole color upper side: Near RHS Greyed-Purple N186C. Petiole color lower side: Near RHS Greyed-Purple N186C. Petiole Texture upper side; Glabrous. Petiole Texture lower side; Glabrous.

*Stipule*.—About 7 mm long and 3 mm wide. Colored near Greyed-Purple N186B.

FLOWER

Natural flowering season: May-June.

Inflorescence type and habit: Terminal and axillary rounded cyme.

Quantity of flowers per inflorescence: Average range 20 to 30.

Inflorescence size:

*Width*.—Approximately 9 cm.

*Height*.—Approximately 7 cm.

Individual flowers:

*Flower form*.—Single whorl of five petals.

*Flower aspect*.—Upright and outward.

*Size*.—Diameter: Approximately 0.9 cm. Length: Approximately 0.7 cm. Persistence: Persistent.

Petal:

*Petal arrangement*.—Whorl.

*Number of petals per flower*.—5.

*Petal appearance*.—Matte.

*Petal shape*.—Obovate.

*Margin*.—Entire.

*Tip shape*.—Obovate.

*Length*.—0.5 cm.

*Width*.—0.3 cm.

*Texture*.—Upper: Glabrous. Lower: Glabrous.

Petal color:

*When opening*.—Upper surface: Outer edge near RHS Red 56B, lower section near Red 56C. Lower surface: Near RHS Red 56D.

*Fully opened*.—Upper surface: Near RHS Red 49D, flushed Red 56C. Lower surface: Outer edge near RHS Red 56C near Red 56D.

*Fading*.—Upper surface: Near RHS White 155A flushed Red 49D. Lower surface: Near RHS White 155A flushed Red 49D.

Petaloids: None present.

Bud:

*Shape*.—Globose.

*Length*.—Approximately 0.5 cm.

*Diameter*.—Approximately 0.4 cm.

*Color*.—Near red 56C flushed Red 55C and 55D.

Sepals:

*Shape*.—Triangular.

*Number of sepals*.—4.

*Arrangement*.—Whorl.

*Length*.—Approximately 0.3 cm.

*Width*.—Approximately 0.1 to 0.2 cm.

*Margin*.—Entire.

*Base*.—Truncate.

*Tip*.—Acuminate.

*Texture*.—Pubescent.

*Color*.—Immature: Near RHS Greyed-Red 179A and 179B. Mature: Near RHS Red 54D flushed Greyed-Red 180D.

Pedicels:

*Length*.—Average 0.7 to 1.1 cm.

*Diameter*.—0.1 to 0.2 cm.

*Color*.—Near RHS Red 54B.

*Orientation*.—Straight.

*Strength*.—Good.

*Texture*.—Glabrous.

REPRODUCTIVE ORGANS

Stamens:

*Number*.—About 20.

*Filament length*.—Approximately 0.3 to 0.4 cm.

*Filament color*.—Near RHS Red 49D.

Anthers:

*Shape*.—Globose.

*Length*.—Less than 0.1 cm.

*Color*.—Immature: Near RHS Red 54A. When Fading: Near RHS Yellow-White 158C.

*Pollen*.—Moderate.

*Pollen color*.—Near RHS Yellow-White 158D.

Pistil:

*Number*.—Average of 4.

*Length*.—Approximately 0.5 cm.

*Style*.—Length: Approximately 0.4 cm. Color: Near RHS Yellow-White 158D.

*Stigma*.—Shape: Club-shaped. Color: Near RHS Yellow-White 158B. Ovary color: Near RHS Yellow-Green 151D.

OTHER CHARACTERISTICS

Seeds and fruits: Three lobed chambers, overall about 6 mm long, 5 mm in diameter. Colored near RHS Red 44A. Seed spherical, less than 0.5 mm in diameter, colored near Orange-White 159A.

Garden performance: Very good.

Disease/pest resistance: Neither resistance nor susceptibility to typical disesases and pests common to *Physocarpus* have been observed.

Temperature tolerance: The new variety tolerates temperatures between −31 to 38° C.

Drought tolerance: Tolerance for drought has not been tested in the new variety. *Physocarpus opulifolis* is typically drought tolerant.

What is claimed is:

1. A new and distinct cultivar of *Physocarpus* plant named 'MINBLA3' as herein illustrated and described.

* * * * *